(12) United States Patent
Deslauriers et al.

(10) Patent No.: US 10,653,804 B2
(45) Date of Patent: May 19, 2020

(54) SOLVENT-FREE GADOLINIUM CONTRAST AGENTS

(71) Applicant: Inventure, LLC, Southbury, CT (US)

(72) Inventors: Richard Deslauriers, Southbury, CT (US); Jonathan Balfour, Toronto (CA); Michael Milbocker, Holliston, MA (US)

(73) Assignee: Inventure, LLC, Southbury, CT (US)

( * ) Notice: Subject to any disclaimer, the term of this patent is extended or adjusted under 35 U.S.C. 154(b) by 0 days.

(21) Appl. No.: 16/537,906

(22) Filed: Aug. 12, 2019

(65) Prior Publication Data

US 2019/0365933 A1 Dec. 5, 2019

Related U.S. Application Data

(60) Division of application No. 16/420,046, filed on May 22, 2019, which is a continuation-in-part of application No. 15/855,570, filed on Dec. 27, 2017, now abandoned.

(60) Provisional application No. 62/439,893, filed on Dec. 29, 2016.

(51) Int. Cl.
*A61K 49/10* (2006.01)
*A61K 49/18* (2006.01)

(52) U.S. Cl.
CPC .......... *A61K 49/105* (2013.01); *A61K 49/108* (2013.01); *A61K 49/18* (2013.01); *A61K 49/101* (2013.01); *A61K 49/103* (2013.01); *A61K 49/106* (2013.01); *A61K 49/1806* (2013.01); *A61K 2123/00* (2013.01)

(58) Field of Classification Search
None
See application file for complete search history.

(56) References Cited

U.S. PATENT DOCUMENTS

| | | | |
|---|---|---|---|
| 10,064,961 B2 * | 9/2018 | Welzig ............... | A61K 49/108 |
| 2011/0129425 A1 * | 6/2011 | Meyer ............... | A61K 49/106 |
| | | | 424/9.363 |

FOREIGN PATENT DOCUMENTS

| | | |
|---|---|---|
| FR | 2927539 | 8/2009 |
| WO | WO 2016/015066 | 2/2016 |
| WO | WO 2016/083605 | 6/2016 |
| WO | WO 2017/046694 | 3/2017 |

OTHER PUBLICATIONS

PCT Search Report and Written Opinion in PCT Application No. PCT/US2017/068534, filed Dec. 27, 2017, dated Mar. 13, 2018.
Brown, "Effects of the Operating Magnetic Field on Potential NMR Contrast Agents" (1985) Magnetic Resonance Imaging, vol. 3, pp. 3-9.
Runge et al., "Paramagnetic Agents for Contrast-Enhanced NMR Imaging: A Review" (1983) American Journal of Radiology, vol. 141, pp. 1209-1215.
Weinman et al., "Characteristics of Gadolinium-DTPA Complex: A Potential NMR Contrast Agent" (1984) American Journal of Radiology, vol. 142, pp. 619-624.
Schmitt-Willich et al., "Synthesis and Physicochemical Characterization of a New Gadolinium Chelate: The Liver-Specific Magnetic Resonance Imaging Contrast Agent Gd-EOB-DTPA" Inorganic Chemistry (1999), vol. 38, pp. 1134-1144.
Gazzi et al., "A greener approach toward gadolinium-based contrast agents" Royal Society of Chemistry, Advances (2014), pp. 9880-9884.
Choi et al., XP002779009 "Process for preparing contrast agent for magnetic resonance imaging" KR 101625656B1 abstract Database WPI.
Jeong et al., "Synthesis of a gadolinium based-macrocyclic MRI contrast agent for effective cancer diagnosis," Biomaterials Research (2018) 22:17.
PCT International Preliminary Report on Patentability issued in PCT Application PCT/US2017/068534, filed Dec. 27, 2017, dated Jul. 11, 2019.

* cited by examiner

*Primary Examiner* — James W Rogers
(74) *Attorney, Agent, or Firm* — Knobbe Martens Olson & Bear LLP

(57) ABSTRACT

Disclosed herein are complexes of gadolinium metal, ligand and meglumine that are substantially free of non-aqueous solvents. In particular, solvent-free complexes of 1) gadopentetate dimeglumine and 2) gadoterate meglumine are disclosed and methods of their preparation are disclosed. In addition, methods are disclosed for purifying reactants, monitoring and controlling pH, quantifying the free gadolinium content, quantifying the concentration of gadolinium-ligand complex in aqueous solution, and procedures for producing a drug product in one step. The one step process eliminates the need to dry the gadolinium-ligand complex, which is typically highly hygroscopic. The one step process includes purification steps that do not require the use of non-aqueous solvents.

17 Claims, 2 Drawing Sheets

SOLVENT-FREE GADOLINIUM CONTRAST AGENTS

CROSS-REFERENCE TO RELATED APPLICATIONS

This application is a divisional of U.S. application Ser. No. 16/420,046, filed May 22, 2019, which is a continuation-in-part of U.S. application Ser. No. 15/855,570, filed Dec. 27, 2017, which claims benefit of U.S. Provisional Application No. 62/439,893, filed Dec. 29, 2016, all of which are hereby incorporated by reference in their entireties.

TECHNICAL FIELD

The present disclosure relates generally to metal chelates, particularly those of lanthanide metals, and in one specific embodiment, those of Gd(III), which are useful as contrast agents in magnetic resonance imaging for therapeutic and diagnostic applications, as well as clinical and biomedical research applications.

BACKGROUND OF THE INVENTION

Magnetic resonance imaging (MRI) is a powerful diagnostic method that yields three-dimensional images of body tissues in vivo. The tissue features obtained are the result of variations in the distribution of water in these tissues. MRI contrast agents administered prior to imaging alter the relaxation times of protons in their vicinity enhancing specific features of an image. MRI contrast agents improve the sensitivity and utility of MRI diagnostics.

The use of contrast agents for MRI in the clinical setting has become a routine standard of practice for the enhancement in resolution and tissue specificity of medical MRI images. Paramagnetic metal chelates, such as Gd(III)-diethylenetriaminepentaacetic acid (Gd(III)-DTPA) (Magnevist), Gd(III)-N,N',N',N'',N'''-tetracarboxymethyl-1,4,7,10-tetraaza cyclododecane (Gd(III)-DOTA), and their analogs have proven to increase the relaxation rate of surrounding protons and have been widely used as MRI contrast agents.

The thermodynamic stability of gadolinium complexes are strongly pH dependent, and while the pH in vivo is not highly variable, the current manufacturing methods yield compositions of gadolinium complexes that vary considerably in pH. Reduced thermodynamic stability can result in the release of toxic Gd(III) ion from the ligand, and may be linked to nephrogenic systemic fibrosis. While the formation of the Gd(III) ion occurs due to manufacturing variations in product pH, and this product pH eventually equilibrates to in vivo pH when injected, the dilution due to injection is sufficiently rapid compared to pH equilibration to separate Gd(III) ion and the ligand (for example, pentetic acid), such that when favorable pH is reached, the metal ion and ligand are sufficiently separated that they do not recombine as a conjugate of ligand and gadolinium.

Consequently, medical contrast agents with a large pH range in the product specification present a safety concern regarding product stability and the potential for formation the release toxic Gd(III) from the complex. The large pH range in the drug product is linked to the use of solvents in the drug purification process, which tends to remove ligand in an unpredictable fashion.

The synthetic methods attempted in the past to prepare paramagnetic metal chelates have one or more drawbacks such as the use of large excess of ligand to reduce free Gd(III) ion; or the need to carry out extensive solvent purification of product due to impurities in the original reagents. Ironically, the biocompatible solvents used to purify the drug product can complex with the impurities they are meant to remove. If pure ingredients are used initially, the need for solvent purification is removed. Nevertheless, solvents are still needed because the gadolinium complex must be precipitated in an anhydrous state in order to formulate the drug product at the therapeutic potency.

The sequence of complexing Gd(III) and the ligand in water, drying, and then reformulating in water is a multi-step process that results in dramatic shifts in the delicate balance between the gadolinium ion and the ligand. Ultimately, this multi-step process is responsible for solvent complexed impurities, shifts in pH and gadolinium-ligand balance. As a consequence, it has become standard in the industry to allow large ranges of pH and meglumine content.

In particular, a significant excess of ligand, for example pentetic acid, is intentionally formulated in the current MRI contrast agent Magnevist®. In Magnevist, the formation of Gd(III) ion is reduced in the presence of excess pentetic acid. The formation of the Gd(III) ion is largely the result of variation in the thermodynamic stability of the macromolecular conjugate of pentetic acid ligand and gadolinium in the presence of solvent.

The shortening of proton relaxation times by gadolinium is mediated by dipole-dipole interactions between the unpaired valence electrons of gadolinium and adjacent water protons. The magnitude of gadolinium magnetic dipole interaction drops off very rapidly as a function of its distance from these protons (as the sixth power of the radius). Consequently, the only protons which are relaxed efficiently are those able to enter the gadolinium metal.

The protons can enter the first or second coordination spheres of the gadolinium metal and metal complex. In coordination chemistry, metal ions are described as consisting of two concentric coordination spheres. The first coordination sphere refers to a central atom or ion (in this case gadolinium). The second coordination sphere can consist of ions (especially in charged complexes), molecules (especially those that hydrogen bond to ligands in the first coordination sphere) and portions of a ligand backbone. Compared to the first coordination sphere, the second coordination sphere has a less direct influence on the reactivity and chemical properties of the metal complex. Nonetheless, the second coordination sphere is relevant to understanding reactions of the metal complex, including the mechanisms of ligand exchange and catalysis.

The protons enter the first or second coordination spheres of the gadolinium metal complex during the interval between an rf pulse and a signal detection. This interval ranges in duration from 105 to 106 protons/second (Brown (1985) Mag. Res. Imag. V 3, p 3).

Gadolinium has seven unpaired valence electrons in its 4f orbital and consequently has the largest paramagnetic dipole (7.9 Bohr magnetons) and exhibits the greatest paramagnetic relaxivity of any element (Runge et al. (1983) Am. J. Radiol V 141, p 1209 and Weinman et al. (1984) Am. J. Radiol V 142, p 619). Consequently, gadolinium has the highest potential of any element for enhancing magnetic resonance images.

In order to take advantage of the large paramagnetic dipole of gadolinium one must recognize the toxicity of free gadolinium metal ion (Gd(III)) in vivo. Thus, the use of gadolinium metal in vivo, for example gadolinium chloride or gadolinium oxide, is not safe and a water-soluble chelate of gadolinium must be used. While a water soluble chelated gadolinium-based contrast agent is safer to inject in patients, the toxicity issues are not entirely solved. Latent toxicity is in part the result of precipitation of the gadolinium that can occur at body pH as gadolinium hydroxide.

However, Gd(III) ion, even if it does not form a water-insoluble compound, can still be toxic, since the reactivity of Gd(III) is very similar to Ca(II), and Ca(II) is ubiquitous in chemical pathways in the mammalian body.

In order to increase solubility and decrease toxicity, gadolinium has been chemically chelated by small organic molecules. To date, the chelator most satisfactory from the standpoints of general utility, activity, and toxicity is diethylenetriamine pentaacetic acid (DTPA) (Runge et al. (1983) Am. J. Radiol V 141, p 1209 and Weinman et al. (1984) Am. J. Radiol V 142, p 619). The first formulation of this chelate to undergo extensive clinical testing was developed by Schering-Berlex AG according to a patent application filed in West Germany by Gries, Rosenberg and Weinmann (DE-OS 3129906 A1 (1981)). The chelate consists of Gd-DTPA which is pH-neutralized and stabilized with an organic base, N-methyl-D-glucamine (meglumine or methyl meglumine).

A direct relationship exists between the concentration of an X-ray attenuator and its efficacy in contrast enhancement. The relationship between concentration and contrast effect is not linear with respect to MRI contrast agents, where a threshold concentration of the paramagnetic entity is required to affect the proton relaxation rates in a physiologic region that is being imaged. Beyond this threshold concentration, any further increase in concentration results in little improvement in contrast enhancement. Thus, MRI contrast agents are formulated as close as practicable to the threshold concentration to help reduce toxic effects not mitigated by chelation. However, if the gadolinium complex is unstable, then the formulation must be hedged and the chelate concentration made greater than the threshold value.

The ionic radii of the trivalent lanthanide cations range from 1.1A for La(III) to 0.85 Å for Lu(III) while Gd(III), sitting exactly in the center of the lanthanide series, has an ionic radius of 0.99 Å, very nearly equal to that of divalent Ca(II). Gd(III) can compete with Ca(II) in the chemical pathways of biological systems, and this substitution potential results in gadolinium toxicity to organisms. In fact, the trivalent ion of gadolinium binds with much higher affinity than the divalent ion of calcium. When bound to a Ca(II)-binding enzyme, lanthanide ion replacement often alters the kinetics of the biological process catalyzed by that enzyme.

The toxicity of gadolinium has placed emphasis on the stability of the gadolinium-ligand (GdL) complex, since the complex form is significantly less toxic than the metal ion form. The thermodynamic stability of a complex simply describes the concentrations of all species present in solution at equilibrium as given by the following equations:

$$Gd(H2O)+L \leftrightarrows GdL(H2O)+7H2O$$

where Gd is gadolinium ion, L is the ligand, K is the stability constant, GdL is the gadolinium-ligand complex, [L] is the ligand protonation constant, [GdL] is the thermodynamic stability constant of the complex, and [Gd] is the Gd(III) ion formation constant. When solvent is introduced into the equilibrium equation, the thermodynamic stability constant of the complex is reduced and the Gd(III) ion formation constant increased.

Free gadolinium metal ion has 8 inner-sphere sites for water, and the complex form has only 1 inner-sphere for water. The Gibbs free energy of the equilibrium process between complex and free metal ion will have large favorable entropy toward the complex form due to the release of seven of the eight inner-spheres for water. This entropy contribution is referred to as the "chelate effect". This chelate effect can be compromised by the presence of solvent, which can form binding spheres with solvent rather than water.

In addition, the gadolinium ion-ligand interaction possesses a large electrostatic component that contributes a favorable enthalpy term. The result is that the overall free energy change becomes quite favorable toward the complex form. For these reasons, the solvated Gd(III) ion forms very stable complexes with ligands having more basic donor atoms. That stability is enhanced by the absence of solvent.

The desirability of maximally basic groups in ligands results in the universal selection of ligands comprised of amines. This consideration also explains why amine groups with amide-containing side-chains are considerably less basic than amine groups with acetate side-chains, for example diethylene triamine pentaacetic acid (DTPA) or pentetic acid.

Higher thermodynamic stability of a complex is expressed by a larger thermodynamic stability constant Kst. It should be appreciated that small differences in the ligand protonation constants can have a significant impact on the thermodynamic stabilities of the resulting GdL complex. Unlike the relatively small variations in the log [L] values for the ligands, the log Kst values for a complex can vary by over 10 orders of magnitude. The stability constant is widely used to compare contrast agents because it reduces comparisons to a single convenient number.

The thermodynamic stability constant describes the equilibrium under conditions where the ligand is entirely deprotonated. At physiological pH values, the ligand will be partially protonated so one can argue that a better way to compare GdL stabilities is to use what are called conditional stability constants, set forth in Table 1.

TABLE 1

Thermodynamic and Conditional Stability Constants for Common Gd Complexes

| Ligand protonation constants | DTPA | DTPA-BMA | DOTA | DOTA-(gly)$_4$ |
|---|---|---|---|---|
| Thermodynamic stability constants pH 14 (log $K_{GdL}$) | 22.46 | 16.85 | 24.7 | 14.54 |
| Conditional stability constant at pH 7.4 (log $K_{eff}$) | 18.4 | 14.8 | 17.2 | 12.7 |

(Schmitt-Willich H, Brehm M, Ewers C L, Michl G, Mueller-Fahrnow A, Petrov O, et al. Inorg Chem 1999; 38: 1134-44.)

Table 1 compares the stability constant of complexes formed between gadolinium and various ligands at pH 14 (deprotonated, and standard "thermodynamic stability constant") and the conditional stability constant at pH 7.4. Stronger acid conditions clearly results in lower complex stability.

There are additional ionic competitors besides protons that can affect complex stability. For instance, ions like zinc, copper, and iron form very stable complexes with these ligands, and can at the right activation energy force gadolinium out of the less toxic complex state. At the same time, gadolinium has a high affinity for some contaminants and will leave the complex for phosphate, citrate, and carbonate ions which may be present in solution. The magnitude of the effect of these contaminants is generally determined by the thermodynamic stability constant at product pH.

Transmetallation of Gadolinium Complexes

Magnevist® list on its label a pH range of 6.5-8 pH. Reported impurities of gadolinium oxide, used in the preparation of Magnevist, are usually 99.9% pure based on the presence of rare earth metals only. Thus the presence of iron, which may be the source of the yellow color, is not assessed. Iron-DTPA complex is yellow in color.

Much attention has been paid to the potential of Zn(II) to react with a gadolinium contrast agent and displace the gadolinium. Such exchange of one metal for another is termed transmetallation. Of the commonly encountered metal ion contaminants in chemical compounds, Na(I), K(I), Mg(II), and Ca(II), all form very weak complexes with the chelators used in contrast agents and are thermodynamically disfavored from such transmetallation reactions. The order of affinity of contrast agent chelators for other endogenous ions is Fe(III)>Cu(II)>Zn(II).

The fact that transmetallation of gadolinium complexes results in the formation of a more unstable metal complex implies that the synthesis methodology can impact the magnitude of transmetallation. In particular, if reaction temperatures are kept as low as possible during the complexation process can significantly reduce the incidence of non-gadolinium metal complex formation.

Accordingly, there is a need to improve the safety profile of MRI contrast agents. The present disclosure addresses this need by providing a gadolinium complex formulation for injection, where solvent is absent, and the competitive interaction with ligand eliminated.

BRIEF SUMMARY OF THE INVENTION

Generally, it is an object of the present invention to provide drug products and methods for synthesizing contrast agents capable of enhancing magnetic resonance images of body organs and tissues, and in particular, a ligand-gadolinium complex possessing an improved safety profile, reduced variability of product and absence of solvent contaminants. Other objects and features will be in part apparent and in part pointed out hereinafter.

Among the several objects of the invention may be noted the synthesis of organic solvent-free complexes of ligand and gadolinium balanced by a counterion, for example meglumine, with only one central metal ion of gadolinium for use in enhancing magnetic resonance images of body organs and tissues.

Another object of the invention is the provision of methods for forming complexes of ligand and gadolinium in a one step process which begins with complex formation and ends with drug product formulation, and beneficially eliminates the use of solvents.

Another object of the invention is to provide a gadolinium contrast agent, such as gadopentetate dimeglumine or gadoterate meglumine, having a pH range that is smaller than currently available formulations.

Another object of the invention is to provide a method of preparation of gadolinium contrast agent formulations in which the formation of non-gadolinium and ligand complexes is reduced significantly or eliminated. In particular, the formation of solvent-ligand complexes is excluded by the present methods.

Another object of the invention is to provide a method of preparation of gadolinium contrast agent formulations with enhanced weights and measures such that the color of the formulation is substantially reproducible and preferably colorless, whereas currently marketed gadopentetate dimeglumine ranges in color from colorless to yellow.

Another object of the invention is the combination of the provisions cited above such that the result is a ligand complex of gadolinium, for example gadopentetate dimeglumine, with a thermodynamic stability of low variability and enhanced stability.

Another object of the invention to provide a solvent-free ligand-gadolinium complex with reduced variability of thermodynamic stability constant, and having a reduced propensity for causing or contributing to a etiology of nephrogenic systemic fibrosis.

Accordingly, the present disclosure provides, a gadolinium contrast agent comprising a complex of Gd(III) ion, ligand and meglumine in a formulation suitable for injection in a mammal, wherein the complex comprises less than 50 parts per million of non-aqueous solvent. In some embodiments, the complex less than 1 part per million of non-aqueous solvent. In some embodiments, the non-aqueous solvent is selected from the group consisting of acetone, methanol, ethanol, heptane, hexane, acetonitrile, toluene or a combination thereof. In more particular embodiments, the solvent is methanol, ethanol, or a combination thereof.

The gadolinium contrast is in some embodiments gadopentetate dimeglumine or gadoterate meglumine.

In certain embodiments, the formulation comprises less than 0.025% by weight of free ligand, and more particularly, less than 0.020%, or 0.010%.

In further embodiments, the formulation has a pH ranging from about 7.2 to about 7.5. In other embodiments, the complex has a thermodynamic stability constant ranging from about 18.1 to about 18.6.

The gadolinium contrast agents of the present disclosure advantageously have reduced impurities. In some embodiments, the contrast agent comprises less than 1 part per million of free Gd(III) ion. In some embodiments, the contrast agent comprises less than 10 parts per million of non-Gd pentetic acid complexes.

The present disclosure further provides a method of synthesizing a gadolinium contrast agent comprising a complex of Gd(III) ion, ligand and meglumine in a formulation suitable for injection in a mammal, wherein the method uses no non-aqueous solvent. The present method advantageously maintains a hydrated state during all of the process steps, meaning that removal of water is not necessary or desired. In some embodiments, the complex is in a hydrated state of at least 1% by weight water during each method step.

In a particular embodiment, the method comprises the steps of: i) preparing an aqueous solution of DOTA, ii) preparing a gadolinium:DOTA complex in water, iii) verifying free gadolinium content in the complex, iv) verifying gadolinium:DOTA complex formation, v) preparing gadoteric acid meglumine solution, and vi) filtering the gadoteric acid meglumine solution. In other embodiments, the method comprises the steps of: i) preparing an aqueous solution of pentetic acid, ii) preparing a gadolinium:pentetate complex in water, iii) verifying free gadolinium content in the complex, iv) verifying gadolinium:pentetate complex formation, v) preparing a gadopentetate dimeglumine solution, and vi) filtering the gadopentetate dimeglumine solution.

The present disclosure further provides a method of reducing the risk of nephrogenic systemic fibrosis in a patient receiving a gadolinium contrast agent comprising administering to the patient a gadolinium contrast agent of claim 1.

DETAILED DESCRIPTION OF THE INVENTION

Disclosed herein is a method of synthesizing solvent-free gadolinium complexes which significantly reduce or eliminate the occurrence of sub-optimal product features that may be linked to adverse clinical outcomes. These sub-optimal product features are: 1) presence of solvent impurities, 2) variation of product pH, 3) variation of product color, 4) variation of product thermodynamic stability constant, 5) formation of free Gd(III) ion and 6) formation of non-gadolinium complexes with pentetic acid.

Figure 1:
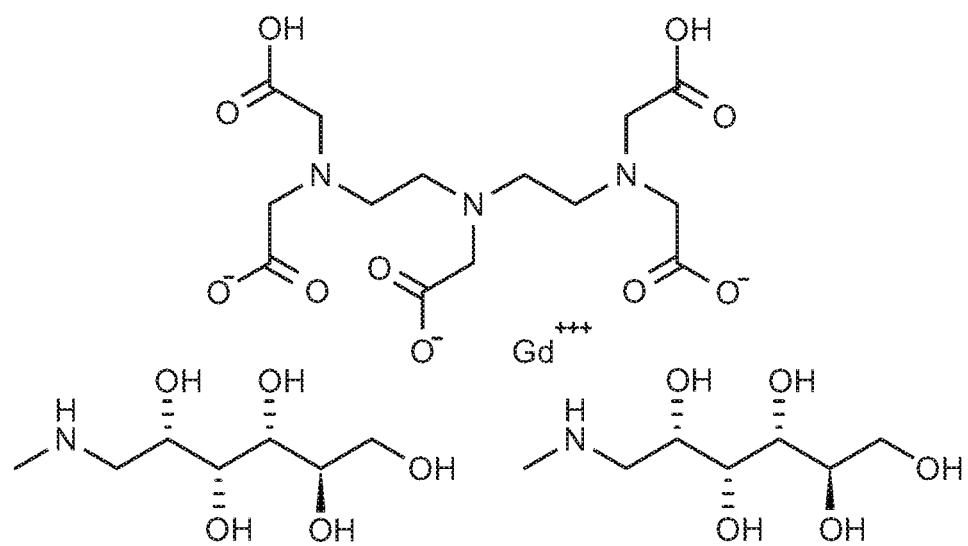
FIG. 1 illustrates the reaction between Gd(III), DTPA, and meglumine to form gadopentetate dimeglumine.

The structure of an example of an enhanced MRI contrast agent of the present invention is provided in FIG. 1. FIG. 1 shows the chemical reactions between one atom of Gd(III), two molecules of DTPA (diethylene triamine pentaacetic acid) and two molecules of meglumine (N-methylglucamine). In steps 1-20 of the present methods, the complex of Gd and DTPA is formed. Concurrently during the complex formation process, the co-ligand (meglumine) is conjugated with the complex for greater stability. The result is gadopentetate dimeglumine (Gd-DTPA-meglumine).

Commercially sold gadopentetate dimeglumine contains 0.027-0.04% non-complexed (excess) pentetic acid contaminant (Sources of Contamination in Medicinal Products and Medical Devices, p. 157, Denise Bohrer). There is no theoretical requirement that this magnitude of excess pentetic acid should be present in commercial formulations of gadopentetate dimeglumine. The common explanation of the excess pentetic acid is that it is provided as a safety feature against the formation of Gd(III) ion. In reality, the excess is there, in part, due to shifts in pH when the dry gadolinium complex is rehydrated.

The thermodynamic stability constants describe the equilibrium between concentrations of the Gd-complex (GdL) on one hand and disassociated concentrations of free Gd(III) and free ligand (L) on the other hand. Since free ligand is far safer than free Gd(III), increasing the concentration of free ligand can inhibit the formation of free Gd(III). In this sense, excess free ligand can be viewed as a safety measure.

In practice it is found that in a closed environment, an increase in the concentration of the free ligand in the formulation of a gadolinium-based contrast agents results in a reduction of the concentration of free Gd(III). This protective effect is more pronounced in the group of linear ligands, in which gadopenteate dimeglumine is a member, and less effective among cyclic ligands. The equilibrium between the concentrations of the GdL complex and the concentrations of the individual complex partners is shifted to the side of the GdL complex through the use of excess ligand to maintain the equilibrium described by the thermodynamic stability constant.

This safety feature is somewhat dubious in that one extremely toxic component is displaced by the existence of a less toxic component, but the highest degree of safety is achieved when the Gd(III) and ligand are perfectly balanced and exist only in the form GdL.

It is natural to consider variations in product pH to be dependent upon how and to what degree the pentetic acid forms the complex with gadolinium. However, in practice variations in final pH are primarily the result of removal of meglumine during the solvent precipitation step. Secondarily, the association of meglumine with the chelate is of interest. And that association can also be affected by the presence of residual solvents. In order to achieve low variance in the product pH, than control of the environment in which the gadolinium-ligand complex is formed is important, and in particular keeping the gadolinium complex in a hydrated state, i.e., in an aqueous solution, can serve to reduce the evolution of anhydride states of the ligand.

Pentetic acid is not an inert chemical compound. Review of the Material Safety Data Sheet reveals that pentetic acid (diethylenetriaminepentaacetic acid) carries several potential health effects:

Potential Health Effects

Inhalation Toxic if inhaled. Causes respiratory tract irritation.

Skin May be harmful if absorbed through skin. Causes skin irritation.

Eyes Causes eye irritation.

Ingestion May be harmful if swallowed

The present invention reduces the amount of intentional excess pentetic acid without increasing the concentration of Gd(III) ion in the product. The general approach to achieving this end is to reduce the variability in parameters that can shift the equilibrium toward Gd(III). The shift toward Gd(III) can result from one or more of the following: 1) metallic contaminants resulting in transmetallation, 2) ionic contaminants resulting in pulling the ligand away from the Gd(III), and 3) a change in the thermodynamic stability constant itself.

Metallic contaminants can be reduced or eliminated in the product by precluding them energetically from forming chelates. In this instance one can take advantage of the preference of amine containing ligands to form complexes with gadolinium before other metals. Thus, precision in controlling the temperature of the reaction, and in particular taking care to avoid activation energies characteristic for common transmetallation reactions, the effect of contaminant induced transmetallation can be significantly reduced.

Ionic contaminants present in the ligand that tend to complex with the ligand by excluding Gd(III) can be reduced by introducing scavenger species, for example carbon filtration) that can bind to the contaminants and which are more easily removed from the reaction than the contaminant moiety.

The thermodynamic stability constant increases (greater stability) as pH rises. A particular ratio of Gd(III) and DTPA is optimal for a given value of thermodynamic stability constant. The practice of intentionally adding excess ligand arises out of the necessity for compensating changes in the thermodynamic stability caused by manufacturing variability of product pH and ligand loss during the usual solvent drying process. Ligand is lost when excess solvent is poured off the crystallized drug product.

The clinical rationale for using excess ligand in gadolinium-based contrast agents is in part based on an increased incidence of NSF(nephrogenic systemic fibrosis) in patients receiving contrast agent. NSF is a very rare disease that, thus far, has predominantly been observed in patients with severe renal impairment. The etiology of NSF is still unknown but is thought to be multifactorial. The particular combination and severity of co-factors necessary to trigger the development of NSF has not, as yet, been elucidated.

Exposure to Gd-based contrast agents (GBCAs) has been identified as a potential risk factor for acquiring this serious and disabling disease. This theory was first proposed in 2006. A number of other mechanisms and potential risk factors have also previously been proposed, including surgery and/or the occurrence of thrombosis or other vascular injury, proinflammatory state, and the administration of high doses of erythropoietin.

Published studies in the medical literature suggest the incidence rates of NSF following theadministration of Magnevist to be lower than that of non-ionic linear GBCAs, ie, Omniscan. Since ionic linear GBCAs are more stable than non-ionic, this suggests NSF may be linked to the thermodynamic stability of metal-ligand complexes contained in GBCAs.

Figure 2:
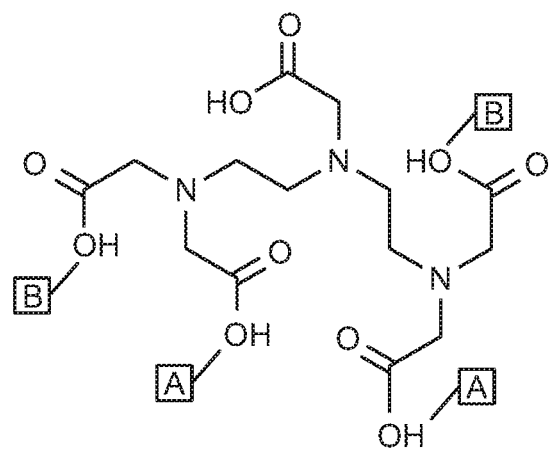
FIG. 2 illustrates the molecular structure of diethylenetriamine pentaacetic acid.
Figure 3:
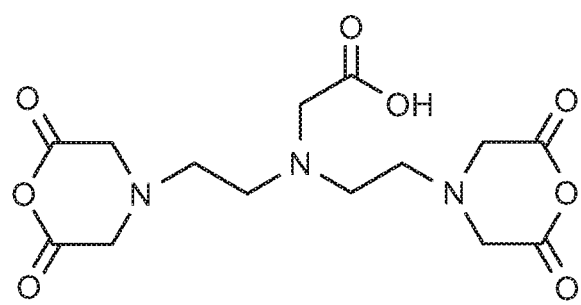
FIG. 3 illustrates the molecular structure of diethylenetriamine pentaacetic dianhydride.

The importance of water in all steps of the drug preparation process can be understood by considering the anhydride state of diethylenetriaminepentaacetic acid. FIG. 2 illustrates the diethylenetriamine pentaacetic acid molecule. The sites A can bond to sites B under anhydrous conditions to form two hexacyclic structures and the release of two molecules of water. The resulting molecule is either diethylenetriamine pentaacetic anhydride, or in saturation diethylenetriaminepentaacetic dianhydride (illustrated in FIG. 3).

The anhydride of diethylenetriaminepentaacetic is less acidic than diethylenetriaminepentaacetic. This can be a source of the observed pH variation of current product pH, and ultimately the cause of variation of the thermodynamic stability constant.

For example, looking at commercial specifications for diethylenetriaminepentaacetic dianhydride (Sigma-Aldrich, St. Louis, Mo.), it can be seen that, depending on the degree of dehydration, diethylenetriaminepentaacetic dianhydride varies in color from colorless to very dark yellow. This observation is consistent with labeling of Magnevist, and suggests some diethylenetriaminepentaacetic dianhydride is present in Magnevist. Further, the source of this contaminant can be associated with the anhydrous precipitation of the gadolinium complex in solvent.

The effect of the presence of diethylenetriaminepentaacetic dianhydride can be seen by considering its acid number: Titration with NaOH 97.5-102.5%.

In a manufacturing process that yields a product that contains diethylenetriaminepentaacetic dianhydride might be titrated down to a pH specification by excess addition of diethylenetriamine pentaacetic after the conjugation step. When the commercial product is formulated, it is formulated in an aqueous state. Consequently, the relatively basic anhydride is converted to the more acidic diethylenetriamine pentaacetic, which reduces the product pH, reduces the thermodynamic stability constant, and results in the formation of Gd(III) ion.

If acid groups are still present in the resulting complex salt, it is often advantageous to convert the acidic complex salt into a neutral complex-salt by reaction with inorganic and/or organic bases or amino acids, which form physiologically biocompatible cations, and isolate them. In many cases, the procedure is unavoidable since the dissociation of the complex salt is moved toward neutrality to such an extent by a shift in the pH value during the preparation that only in this way is the isolation of homogeneous products or at least their purification made possible. Production is advantageously performed with organic bases or basic amino acids. It can also be advantageous, however, to perform the neutralization by means of inorganic bases (hydroxides, carbonates or bicarbonates) of sodium, potassium or lithium.

The present novel method for synthesis of gadopentetate dimeglumine encompasses all the considerations described above to provide a product that: 1) contains no solvent residues, 2) possesses a product pH variation in the range of 7.2 to 7.5, 3) is colorless, 4) possesses a product thermodynamic stability constant variation in the range of 18.2-18.6, 5) less than 1 ppm free Gd(III) ion and 6) less than 10 ppm non-gadolinium complexes with pentetic acid.

The present methods advantageously take aqueous solution to a drug product concentration and purity, without the need to obtain a dry powder of gadolinium complex is advantageous. The absence of organic solvent in the drug product is a distinguishing characteristic of the present novel drug compounds. In practice, it is impossible to remove all solvent from a gadolinium contrast agent when a solvent other than water is used during synthesis. All present gadolinium contrast agents have measureable solvent contaminations; and in most commercial products one or more solvents represent the most impurities.

Generally, contrast agents of the invention may be preformed, or may alternatively be prepared directly before administration, by mixing in aqueous solution the chelating agent and a soluble compound containing the paramagnetic metal with a physiologically acceptable counter ion. Generally, the chelating entity is itself in salt form. The counterion should also be physiologically acceptable and may, for example, be meglumine.

Furthermore, solvents such as acetone, various alcohols, heptane and the like form complexes with naturally occuring impurities present in the ligand. The solvents intended to create a crystalline pure drug compound ironically bind impurities in the drug product. Ultimately, the solvents primarily serve as azeotropic agents for removing water and not as purifying agents. Solvents are not used in the present invention.

The product gadopentetate dimeglumine is hygroscopic and difficult to separate from the water used in the synthesis. The final product form is formulated as an aqueous solution. Consequently, it is important to determine the final mass or mass proportion of gadopentetate dimeglumine in a batch output. This can be done using the HPLC analysis techniques disclosed here. It is a simple matter to determine how much additional water is to be added to a particular hydrated batch product to obtain a desired product formulation specification.

Examples

In the following, absolute weights of ingredients and volumes of the equipment used are illustrative only, and it should be understood that it is the mass ratios between ingredients that is the important aspect of this invention. Those ingredients are given in the Table below.

| Ingredient | Mol. Wt. | Amount | Equivalents | Amount in Example |
|---|---|---|---|---|
| DTPA | 393.35 | 1 mole | 393.35 g/mol | 393.35 kg |
| Gd(III) oxide | 362.50 | ½ mole | 181.25 g/mol Gd | 181.25 kg |
| n-methylglucamine | 195.21 | 2 moles | 390.42 g/mmol | 390.42 kg |

The following procedure is the result of complicated equilibria calculations involving the calculation of protonation constants, thermodynamic stability constants, and equilibrium speciation diagrams.

Purification of Ligand

As an example, a procedure for purification of DTPA is provided. It should be understood the procedure is applicable to all ligands used in forming complexes of gadolinium useful as contrast agents in medical imaging.

In a 5.0 litre four neck round bottom flask equipped with a mechanical stirrer, condenser and heating jacket was charged 3000 ml of distilled water (pH 7) and 500 g of DTPA at 25 to 30° C.

After stirring for 10 minutes, raise the temperature of the reaction mixture to 95-100° C., stir until the mixture forms a clear solution and maintain at this temperature for 0.5 hrs after forming clear solution.

Cool the reaction mixture to 35-40° C. and stir for 1 h. The DTPA should precipitate out of solution as a crystallite.

Filter the slurry through a Buchner funnel and wash with distilled water. Perform HPLC and quantify impurities, total impurities should be less than 0.5% N/N. If not, return to step 1.

Dry the purified DTPA under reduced pressure at 55-60° C. for 1 h.

Determination of % Free Ligand

It is important to determine the amount of free ligand in the complexation synthesis between gadolinium and ligand. In this example, an HPLC procedure is provided for determining % w/w of free DTPA compared to the weight of the complex in a solution of gadolinium-DTPA complex.

Chromatographic System:
Instrument: Agilent 1200 Series (or) equivalent
Column: Hypersil MOS-1, 150×4.6 mm, 5 μ
Wavelength: 195 nm
Mobile Phase:
Pump 'A': 10 mM potassium phosphate monobasic in water, pH 3.0 with Orthophosphoric acid (0.1 M)
Pump 'B': 1.5 mM Tetra-n-butylammonium perchlorate in Acetonitrile:Water (20:80)
Isocratic: A:B (30:70)
Flow Rate: 1.5 ml/min
Column oven: 25° C.
Injection Volume: 20 μl
Run Time: 20 minutes
Diluent: Water Definitions:
Purity: The mass amount of gadopentetate dimeglumine relative to other HPLC peaks. The purity is not specific to dilution, the amount of water in the sampled API does not change the purity.

Wet API sample Potency: The mass amount of gadopentetate dimeglumine API in a mass amount of diluent, usually water. Applies to in-process/wet API.

General Notes:
The following flask sizes and standard weights may be adjusted as long as the final concentration of each solution is maintained. Sonication or other appropriate means may be used to aid dissolution. Mix each solution until all solids are dissolved.

DTPA Standard Preparation:
Prepare a solution containing 0.0033 mg/ml of purified DTPA in diluent. Weigh about 0.33 mg of DTPA in a 100 ml volumetric flask, add 10 ml of diluent, gently warm up to 60 degree in water bath and allow to cool. Swirl to dissolve. Bring up to volume with water.

API Sample Preparation (Wet or Dry):
Prepare a solution that yields a product value=(API concentration (mg/ml)×Wet API Potency) in the range of 5-10 mg/ml of API in water. In other words, when the solution is made it should satisfy:

5<(API concentration (mg/ml)×Wet API Potency)
<10 mg/ml of API in water

Weigh about 500.0×(1/Potency) mg of API in a 100 ml volumetric flask, add 10 ml of diluent, mix thoroughly. Bring up to volume with diluent. Assess by HPLC that the concentration of Gadopentetate dimeglumine meets target specification.

Evaluation of System Suitability:
DTPA retention time should be about 4.5 minutes. The chromatographic procedure is set forth in the following table:

| Description | #Injection |
| --- | --- |
| Blank | 3 |
| DTPA Standard | 5 |
| API solution | 2 |

The gadopentetate dimeglumine peak will be quite large in the API sample, the mV scaling of the HPLC should be adjusted so that the DTPA peak is discernible. It should be verified visually that the DTPA peak and the Gadopentetate Dimeglumine peak in the API sample do not overlap. Overlap will give an erroneous integrated area.

Reporting Criteria:
Integrate only the DTPA peaks in the DTPA standard and API. Calculate % Free DTPA relative the API (w/w) using one the following equations:

% Free DTPA/Wet API sample (w/w)=Area API DTPA peak×Std DTPA Concentration (mg/ml)× Purity DTPA×100%/Mean peak area DTPA standard (n=5)×API concentration (mg/ml)    (1)

% Free DTPA/API (w/w)=(1)×(1/Wet API Potency)    (2)

Potency is obtained from the API HPLC Potency Procedure.

Determination of Potency of Gadolinium-Ligand Complex.
In this example, an HPLC procedure is provided for determining % w/w of gadolinium-ligand complex compared to the weight of the solution of gadolinium-DTPA complex. This method determines the chromatographic potency of gadopentetate dimeglumine drug substance by HPLC with UV detector:

Chromatographic System:
Instrument: Agilent 1200 Series (or) equivalent
Column: Hypersil MOS-1, 150×4.6 mm, 5 μ
Wavelength: 195 nm
Mobile Phase:
Pump 'A': 10 mM potassium phosphate monobasic in water, pH 3.0 with dilute orthophosphoric acid (0.1 M)
Pump 'B'
Isocratic: A:B (30:70)
Flow Rate: 1.5 ml/min
Column oven: 25° C.
Injection Volume: 20 μl
Run Time: 20 minutes
1.5 mM Tetra-n-butylammonium perchlorate in Acetonitrile:Water (20:80)

The following flask sizes and standard weights may be adjusted as long as the final concentration of each solution is maintained. Sonication or other appropriate means may be used to aid dissolution. Mix each solution until no solid remains.

Stock Standard preparation:

Prepare a solution containing 0.5 mg/ml of Gadopentetate Dimeglumine standard in diluent. For example, weigh about 50.0 mg of Gadopentetate Dimeglumine standard in a 100 ml volumetric flask, add 30 ml of diluent, and gently swirl to dissolve and dilute to volume with diluent.

Working Standard Preparation:

Prepare a solution containing 0.005 mg/ml of Gadopentetate Dimeglumine standard in diluent. Pipette 2.0 ml into a 200 ml volumetric flask, add diluent to mark and mix well.

Sample Preparation (API):

Prepare a solution containing 5.0 mg/ml of sample in diluent. Weigh about 100.0 mg of sample in a 20 ml volumetric flask, add 10 ml of diluent and gently swirl to dissolve. Bring up to volume with diluent.

Evaluation of System Suitability:

% RSD for retention time for the first 5 injections of standard solution is not more than 2.0%. % RSD for peak area for the first 5 injections and throughout the run of standard solutions is not more than 15%. Diluent peak should not show any interfering peaks at retention time of Gadopentetate peak greater than 5% of the peak area response of Gadopentetate peak from the analysis of the working standard. Tailing factor for the working standard solution should not be more than 2, assess based on the 1st Injection of working standard solution.

Integrate only the gadopentetate dimeglumine peaks in the sample and in the working standard.

Calculate the Potency (% w/w) of gadopentetate dimeglumine API in the Wet API sample using the following equation:

Potency API/Wet API sample (% w/w)=Area Gad. Dimeg. peak in Sample×Standard Concentration (mg/ml)×100%/Mean peak area of working standard (n=5)×sample concentration (mg/ml)

Determination of Purity of Gadolinium-Ligand Complex

In this example, an HPLC procedure is provided for determining % w/w of non-complex moieties (impurities) compared to the weight of the complex in a solution of gadolinium-DTPA complex. This method determines the chromatographic purity of Gadopentetate Dimeglumine drug substance by HPLC with UV detector:

Column: Hypersil MOS-1, 150×4.6 mm, 5 μm, Part#30205-154630

Purified Water or HPLC Grade, Fisher Scientific Cat#W5-4 or equivalent

Acetonitrile, HPLC Grade, Fisher Scientific Cat#A996-4 or equivalent

Tetra-n-butylammonium Perchlorate, Alfa-Aesar Cat#30801 or equivalent

Potassium Phosphate monobasic, ACS grade, BDH Cat#BDH9268 or equivalent

Phosphoric Acid, HPLC grade, EMD Cat#PX0996-6 or equivalent

Meglumine (N-Methylglucamine), Acros Organics Cat#126841000 or equivalent

Gadopentetate Dimeglumine Reference Standard

Analytical Balance capable of reading 0.01 mg

Calibrated pH meter

Class "A" volumetric glassware

Solution Preparations

Dilute Phosphoric Acid: Pipette 5.0 mL of Phosphoric acid into a 50-mL volumetric flask and dilute to volume with purified water, mix well.

Mobile Phase A: (10 mM Potassium Phosphate monobasic in water) Weigh accurately 1.36 g of Potassium phosphate monobasic (KH2P04) and transfer into a 1 L HPLC bottle already containing 1000 mL of water and mix well. Scale up the volume as required. Adjust to pH 3.0 using dilute phosphoric acid.

Mobile Phase B: (1.5 mM Tetra-n-butylammonium perchlorate in Acetonitrile: Water/20:80) Weigh and transfer accurately 0.51 g of tetra-n-butylammonium perchlorate into a 1 L HPLC bottle. Add 200 mL acetonitrile and dissolve the solids. Add 800 mL of purified water and mix it well. Scale up the volume as required.

Diluent: Purified or HPLC grade water.

Meglumine 41.5% Solution: weigh about 41.5 mg of Meglumine in to a 20-mL volumetric flask. Dissolve and dilute to mark with diluent and mix well.

Note: Use Anti-static gun to remove charge from spatula, hand gloves, sample standard bottle and weighing pan or volumetric flasks while weighing gadopentetate dimeglumine standard and sample.

Stock Standard Preparation (0.5 mg/mL)

Weigh accurately 50 mg±1 mg of Gadopentetate Dimeglumine Reference Standard into a 100-mL volumetric flask. Add approximately 30 mL of diluent to the flask and gently swirl or vortex to dissolve. Bring up to volume with diluent. Sonicate for about 5 minutes, if necessary, to ensure complete dissolution of the material. Allow to cool to room temperature and Mix the solution well. Stock Standard Concentration (mg/mL)=Standard Weight (mg)×Decimal Purity/100 mL Working Standard Preparation (0.005 mg/mL)

Accurately pipette 2.0 mL of Gadopentetate Dimeglumine stock Standard into a 200 mL volumetric flask. Add diluent to the mark and mix well. Transfer the standard solution into HPLC vial and seal for analysis. Working Standard Concentration (mg/mL)=Stock standard concentration (mg/ml)×2.0 mL/200 mL.

Sample Preparations

Weigh 100 mg±1 mg of Gadopentetate Dimeglumine sample into a 20-mL volumetric flask. Add approximately 10 mL of diluent to the flask and gently swirl or vortex to dissolve. Bring up to volume with diluent. Sonicate for about 5 minutes, if necessary, to ensure complete dissolution of the material. Allow to cool to room temperature and mix the solution well. Transfer the sample solution into a HPLC vial and seal for analysis. Sample Concentration (mg/mL) =Sample Weight (mg)/20 mL.

Instrument Operating Conditions

Typical starting column pressure is approximately 96 bar.

| Mobile Phase: | A. 10 mM Potassium Phosphate monobasic in Water |  |  |
|---|---|---|---|
|  | B: 1.5 mM TBAP in Acetonitrile: Water/20:80 |  |  |
| Mobile Phase ration (Isocratic): | Time | Solvent A (%) | Solvent B (%) |
|  | 0 | 30 | 70 |
|  | 15 | 30 | 70 |
| Flow Rate: |  | 1.5 mL/min |  |
| Total Run Time: |  | 20 min |  |
| Column Temperature: |  | 25° C. |  |
| Detection Wavelength: |  | 195 mm |  |
| Injection Volume: |  | 20 μl |  |

Operating Procedure
  Injection Sequence:
  (Inject Standard Solution after every 5 sample preparation injections.)
   1. Blank (3×, at least to ensure a clean baseline)
   2. Working Standard Solution (5×)
   3. Meglumine 41.5% Solution (1×)
   4. Blank (1×)
   5. Sample Solution (2×, for each sample)
   6. Blank (1×)
   7. Standard Solution (1×)
System Suitability
   1. Diluent blank does not show any interfering peaks at retention time of Gadopentetate peak greater than 5% of the peak area response of Gadopentetate peak from the analysis of the working standard solutions.
   2. Tailing factor for the working standard solution is NMT 2; assess based on the 1st injection of working standard solution.
   3. % RSD for Retention time for the first 5 injections of Standard Solutions is NMT 15%.
   4. % RSD for Peak area for the first injections and throughout the run of Standard Solutions is NMT 15.
  Calculations
   1. Integrate all peaks excluding peaks present in blank and Meglumine 41.5% solution injection (Meglumine and related peaks).
   2. Calculate % Weight of Gadopentetate Dimeglumine related substances using the following equation:

% Wt/Wt=Peak area of related substances×Standard Concentration (mg/mL)×100%/Mean Peak area of working standard (n=6)×Sample Concentration (mg/mL)

Example 1: Solvent-Free Gadopentetate Dimeglumine

Raw Materials

|   | Raw Material | Mole Ratio |
|---|---|---|
| 1 | DTPA | 1 |
| 2 | Gd$_2$O$_3$ | 0.496 |
| 3 | Water | 2.2V$^1$ (DTPA) |
| 4 | Meglumine | 0.992 |

Figure 4:
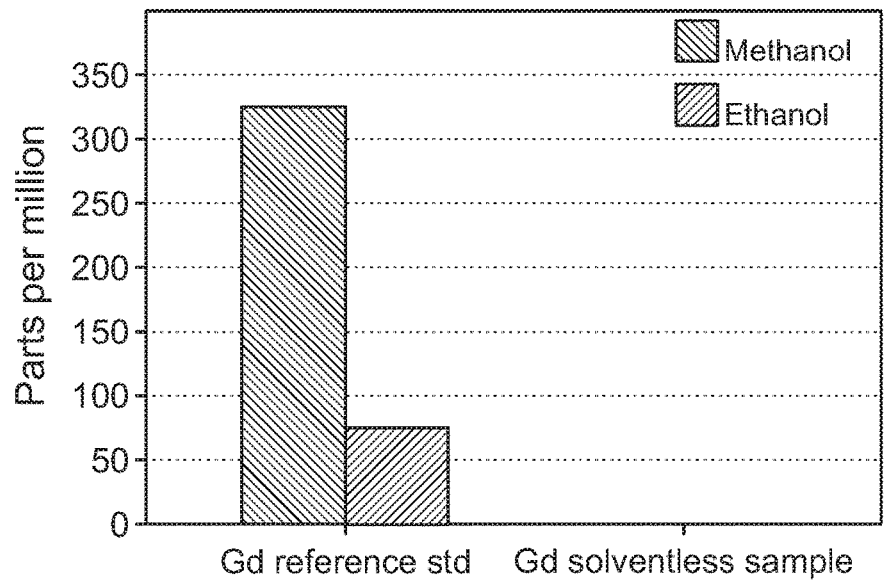
FIG. 4 is a graph comparing the amount of methanol and ethanol in a commercially available gadopentate dimeglumine formulation and a gadopenteate dimeglumine formulation prepared according to the present disclosure.

Preparation of DTPA Solution
   1. Heat reactor to 25-30° C.
   2. Charge water
   3. Begin stirring (stir unless otherwise indicated, nominal rate 300 rpm)
   4. Charge 10% of the DTPA
   5. Stir until uniformly distributed in the water
   6. If all the DTPA is charged, then go to step 8
   7. Go to step 4
   8. Stir 10 min
Preparation of Gadolinium: DTPA Complex
   9. Charge 25% by weight of the Gadolinium oxide
   10. Stir until uniformly distributed
   11. If all the Gadolinium oxide is charged then go to step 13
   12. Go to step 9
   13. Stir 10 min
   14. Raise temperature to 95+/−2° C.
   15. Stir 3 hrs.
   16. Check clarity
   17. If not clear continue for 1 hr, go to step 16
   18. If clear, continue 1 hr and then cool to 40-45° C.
   19. If precipitate forms, heat to 95+/−2° C. and stir for 1 hr, go to step 16
Verify Complex Formation
   20. Verify absence of free gadolinium using Xylenol orange
   21. If free gadolinium detected, add 0.05% additional DTPA, raise temperature to 95−/−2° C., stir for 1 hr and proceed to step 16
   22. If not, proceed to step 23
Preparation of Gadopentetate Dimeglumine solution
   23. Add 90% of the Meglumine at 40-45° C.
   24. Stir until in solution ~1 hr
   25. Measure pH—inline probe calibrated to 25° C. (USP)
   26. If pH is >7.5, discard
   27. If pH is between 7.0 and 7.5, then go to step 29
   28. If pH<than 7.0, add 1% of the Meglumine, stir for 10 min, go to step 25
   29. Stir for 1 hr at 40-45° C.
   30. Check solution is clear, if yes proceed to 31, if not repeat 29
Gadopentetate Dimeglumine Solution Filtration
   31. Measure pH—inline probe calibrated to 25° C. (USP)
   32. If pH is between 7.0 and 7.5, then go to step 34
   33. If pH<than 7.0, add Meglumine, stir for 10 min, go to step 31
   34. Filter the solution using the carbon filter
   35. Rinse the reactor with 20-25° C. water using ¼ V
   36. Pass rinse through the filter
   37. Repeat rinse steps 35 & 36 for a total of 2 rinses
   38. Place filtrate and rinses back in reactor
   39. Stir at 40-45° C. for 10 min
   40. Verify absence of free gadolinium using Xylenol orange
   41. If free gadolinium detected, add 0.05% additional DTPA, stir for 1 hr, and go to step 40
   42. If not, proceed to step 43
   43. Measure pH—inline probe calibrated to 25° C. (USP)
   44. If pH is between 6.0 and 6.6, then go to step 46
   45. If pH<6.0, add Meglumine. Stir 10 min. Go to step 43.
   46. Stir ½ hr.
   47. Check solution is clear, if yes proceed to 48, if not go to step 46
Verify Purity
   48. Measure Purity by HPLC
   49. If individual impurity>0.05%, go to step 31
Final API Adjustments
   50. Measure Free DTPA by HPLC
   51. If Free DTPA>0.06% ww, go to step 31
   52. If Free DTPA is 0.01-0.06% ww proceed to 56
   53. If Free DTPA<0.01% ww, add 0.05% of DTPA
   54. Stir 1 hr
   55. Go to Step 50
   56. Measure pH
   57. If pH is 6.0-6.6, then go to step 59
   58. If pH<6.0, add Meglumine. Stir 10 min. Go to step 56
Final API Testing
   59. Perform full API testing: Gadolinium content; Meglumine Content; Assay; Water Content; Heavy Metals
Comparison: Present Invention and Magnevist
   The brand name for Gadopentetate Dimeglumine is Magnevist. Using HPLC, direct comparison of solvent content in Magnevist can be made to the present invention. FIG. 4 depicts a representative sample of the parts per million of solvent in commercially available Magnevist. By not using solvents in the manufacturing process the amount of all impurities (including non-solvent impurities) is improved.

Figure 5:
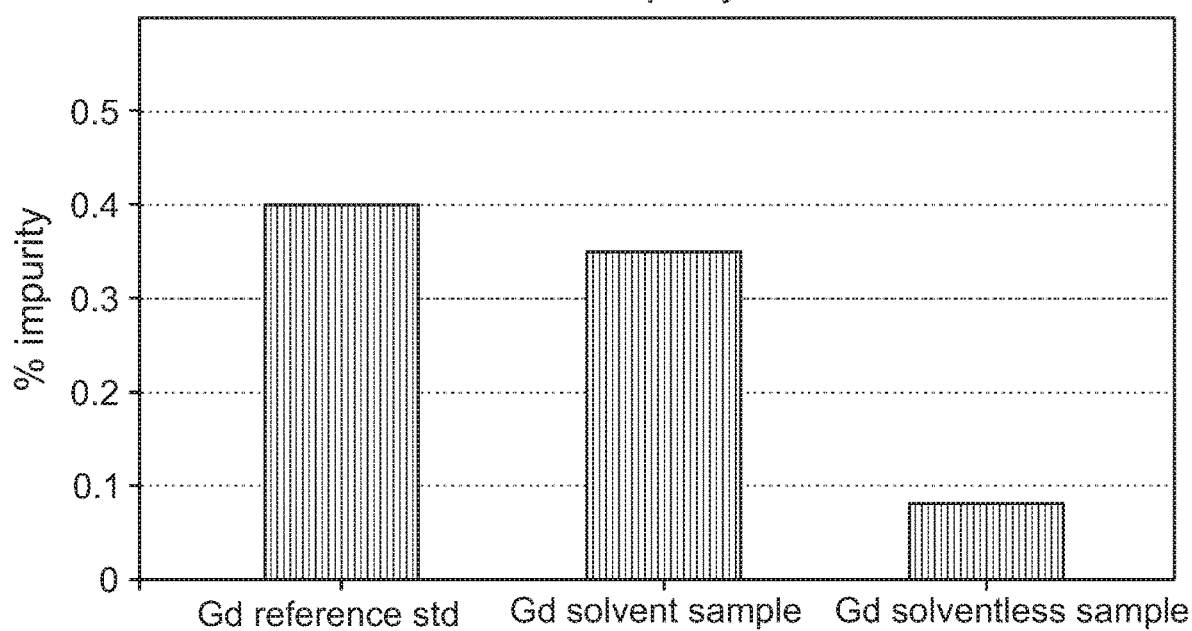
FIG. 5 is a graph comparing the impurity content of a commercially available gadopentate dimeglumine formulation to a gadopenteate dimeglumine formulation prepared according to the present disclosure.

In FIG. 5, the impurity content of Magnevist (Gd reference std) is compared to the complex of the present invention "purified" with solvents (Gd solvent sample) and using the solvent-free procedure (Gd solventless sample). These data illustrate an overall improvement in impurity levels when solvents are removed from the drug product process.

Example 2: Solvent-Free Gadoterate Meglumine

Preparation of DOTA Solution
1. Heat reactor to 25-30° C.
2. Charge water
3. Begin stirring (stir unless otherwise indicated, nominal rate 300 rpm)
4. Charge 10% of the DOTA (1,4,7,10-tetraazacyclodo-decane-1,4,7,10-tetraacetic acid)
5. Stir until uniformly distributed in the water
6. If all the DOTA is charged, then go to step 8
7. Go to step 4
8. Stir 10 min Preparation of Gadolinium: DOTA Complex
9. Charge 25% by weight of the Gadolinium oxide
10. Stir until uniformly distributed
11. If all the Gadolinium oxide is charged then go to step 13
12. Go to step 9
13. Stir 10 min
14. Raise temperature to 95+/−2° C.
15. Stir 3 hrs.
16. Check clarity
17. If not clear continue for 1 hr, go to step 16 (this step took about 12 hours, slower than Magnevist synthesis)
18. If clear, continue 1 hr and then cool to 40-45° C.
19. If precipitate forms, heat to 95+/−2° C. and stir for 1 hr, go to step 16

Verify Complex Formation
20. Verify absence of free gadolinium using Xylenol orange
21. If free gadolinium detected, add X DOTA, raise temperature to 95+/−2° C., stir for 1 hr and proceed to step 16
22. If not, proceed to step 23

Preparation of Gadolinium: DOTA Complex
23. Add 90% of the Meglumine at 40-45° C.
24. Sir 10 minutes
25. Measure pH—inline probe calibrated to 25° C. (USP)
26. If pH is>7.5, discard
27. If pH is between 7.0 and 7.5, then go to step 29
28. If pH<than 7.0, add 2% of the Meglumine, go to step 24
29. Stir for 1 hr at 40-45° C.
30. Check solution is clear, if yes proceed to 31, if not repeat 29

Gadoteric Acid Meglumine Solution Filtration
31. Cool the solution to 20-25° C.
32. Filter the solution using the carbon filter
33. Rinse the reactor with 20-25° C. water using ¼ V
34. Pass rinse through the filter
35. Repeat rinse steps 33 & 34 for a total of 2 rinses
36. Place filtrate and rinses back in reactor
37. Stir at 25-30° C. for 10 min
38. Measure Free DOTA by HPLC
39. If Free DOTA is 0.01-0.06% ww proceed to 42
40. If Free DOTA<0.01% ww, add 0.03% ww equivalent of DOTA
41. Stir for ½ hr and go to step 38
42. Measure pH—inline probe calibrated to 25° C. (USP)
43. If pH is between 7.0 and 7.5, then go to step 45
44. If pH<7.0, add Meglumine. Stir 10 min. Go to step 42.
45. Stir ½ hr.
46. Check solution is clear, if yes proceed to 47, if not repeat 45

Verify Purity
47. Measure Purity by HPLC
48. If individual impurity>0.05%, go to step 32

Final API Adjustments
49. Measure Free DOTA by HPLC
50. If Free DOTA>0.06% ww, repeat steps 32-42
51. If Free DOTA is 0.01-0.06% ww proceed to 55
52. If Free DOTA<0.01% ww, add 0.03% ww equivalent of DOTA
53. Stir ½ hr
54. Go to Step 49
55. Measure pH
56. If pH is 7.0-7.5, then go to step 53
57. If pH<7.0, add Meglumine. Stir 10 min. Go to step 55

Final API Adjustments
58. Perform full API testing: Gadolinium content; Meglumine Content; Assay; Water Content; Heavy Metals The effect of reaction time on free Gd (III) ion content was evaluated by carrying out reactions as described above for various periods of time. The free Gd (III) ion content was determined using the xylenol orange method. See Jeong, Y. and Na, K., "Synthesis of a gadolinium based-macrocyclic MRI contrast agent for effective cancer diagnosis," *Biomaterials Research* (2018) 22:17. The resulting aqueous formulations, comprising a complex of Gd(III) ion, ligand and meglumine, contained not more than 0.025% by weight of free ligand, less than 50 parts per million of non-aqueous solvent, and various amounts of free Gd (III) ion. The results tabulated below show that reactions as described above can be used to obtain such formulations having a broad range of levels of free Gd (III) ion, such as less than 10,000 ppm, less than 5,000 ppm, less than 1,000 ppm, less than 500 ppm, less than 100 ppm, less than 25 ppm, less than 10 ppm, less than 5 ppm, less than 1 ppm, less than 0.5 ppm, or less than 0.1 ppm, by controlling the reaction time.

| Reaction Time, hr | Free Gd(III), ppm |
|---|---|
| 3 | 28,094 ± 9.7 |
| 8 | 3,853 ± 12.4 |
| 24 | 72 ± 5.0 |
| 32 | 0.8 ± 1.3 |

Production of a medical contrast media according to the invention can be clinically formulated in a way known in the art. For example, the gadopentetate dimeglumine solution is diluted in an aqueous medium and then the solution or suspension is sterilized. Suitable additives include, for example, physiologically biocompatible buffers (as, for example, tromethamine hydrochloride), slight additions of complexing agents (as, for example, DTPA) or, if necessary, electrolytes (for example, sodium chloride).

Preferred embodiments of this invention are described herein. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of making a gadolinium contrast agent, comprising:

reacting a ligand with Gadolinium Oxide in water at a reaction temperature and for a reaction time of at least twelve hours to thereby provide a Gadolinium:ligand complex; and reacting the Gadolinium:ligand complex with meglumine to thereby provide a complex of Gd(III) ion, ligand and meglumine in an aqueous formulation;

wherein:

the aqueous formulation comprises not more than 0.025% by weight of free ligand;

the aqueous formulation comprises less than 100 parts per million of free Gd(III) ion; and the aqueous formulation comprises less than 50 parts per million of non-aqueous solvent.

2. The method of claim 1, wherein the aqueous formulation comprises less than 10 parts per million of free Gd(III) ion.

3. The method of claim 1, wherein the aqueous formulation comprises less than 5 parts per million of free Gd(III) ion.

4. The method of claim 1, wherein the aqueous formulation comprises less than 1 part per million of free Gd(III) ion.

5. The method of claim 1, wherein the aqueous formulation comprises less than 0.5 part per million of free Gd(III) ion.

6. The method of claim 1, wherein the aqueous formulation comprises less than 1 part per million of non-aqueous solvent.

7. The method of claim 1, wherein the complex is gadopentetate dimeglumine.

8. The method of claim 1, wherein the complex is gadoterate meglumine.

9. The method of claim 1, wherein the aqueous formulation comprises less than 0.020% by weight of free ligand.

10. The method of claim 1, wherein the aqueous formulation has a pH in the range of from about 7.2 to about 7.5.

11. The method of claim 1, wherein the complex has a conditional thermodynamic stability constant, at pH 7.4, in the range of from about 18.1 to about 18.6.

12. The method of claim 7, wherein the aqueous formulation comprises less than 10 parts per million of non-Gd pentetic acid complexes.

13. The method of claim 1, wherein the reaction time is at least 24 hours.

14. The method of claim 1, wherein the reaction time is at least 32 hours.

15. The method of claim 1, wherein the reaction temperature is about 95° C.

16. The method of claim 3, wherein the reaction time is at least 16 hours and the aqueous formulation comprises less than 5 parts per million of free Gd(III) ion.

17. The method of claim 1, wherein the reaction time is at least 24 hours and the aqueous formulation comprises less than 1 part per million of free Gd(III) ion.

* * * * *